United States Patent [19]
Van Den Broek et al.

[11] Patent Number: 6,090,607
[45] Date of Patent: Jul. 18, 2000

[54] ENHANCED EXPRESSION OF PROTEOLYTIC ENZYMES IN KOJI MOLD

[75] Inventors: Peter Van Den Broek, Epalinges; Michael Affolter, Pully, both of Switzerland

[73] Assignee: Nestec S.A., Vevey, Switzerland

[21] Appl. No.: 09/254,325

[22] PCT Filed: May 1, 1998

[86] PCT No.: PCT/EP98/02785

§ 371 Date: May 17, 1999

§ 102(e) Date: May 17, 1999

[87] PCT Pub. No.: WO99/02691

PCT Pub. Date: Jan. 21, 1999

[30] Foreign Application Priority Data

Jul. 5, 1997 [EP] European Pat. Off. ............... 97111378

[51] Int. Cl.$^7$ .................................... C12N 9/58
[52] U.S. Cl. .......................... 435/223; 435/183; 435/195; 435/212; 435/219; 435/254.1; 435/254.11; 435/254.3; 435/254.8; 435/254.9; 435/69.1; 435/71.1
[58] Field of Search .................. 435/69.1, 71.1, 435/183, 195, 212, 219, 223, 254.1, 254.11, 254.3, 254.8, 254.9

[56] References Cited

U.S. PATENT DOCUMENTS 4,308,284  12/1981  Noda et al. ................................. 426/7

FOREIGN PATENT DOCUMENTS

| 417 481 A1 | 8/1990 | European Pat. Off. . |
| 429 760 B1 | 8/1990 | European Pat. Off. . |
| 818 153 A1 | 7/1996 | European Pat. Off. . |
| WO 95/35385 | 12/1995 | WIPO . |
| WO95/35385 | 12/1995 | WIPO . |

OTHER PUBLICATIONS

Kudla et al. The EMBO Journal. vol. 9(5), pp. 1355–1364, 1990.
Stankovich et al. Molecular Microbiology. vol. 7(1), pp. 81–87, 1993.
Kudla, Bernard et al. XP000615427. "The regulatory gene areA mediating nitrogen metabolite repression in *Aspergillus nidulans*. Mutations affecting specificity of gene activation alter a loop residue of a putative zinc finger". The EMBO Journal vol. 9 No. 5 pp. 1355–1364, 1990.
Stankovich, M. et al. XP002048815. "C–terminal truncation of the transcriptional activator encoded by areA in *Aspergillus nidulans* results in both loss–of–function and gain–of–function phenotypes". Molecular Microbiology (1993) 7(1) pp. 81–87.
Platt, Adam et al. XP002077390. "Nitrogen metabolite signaling involves the C–terminus and the GATA domain of the Aspergillus transcription factor AREA and the 3 ' untranslated region of its mRNA". The EMBO Journal vol. 15 No. 11 pp. 2791–2801, 1996.
van den Hombergh, Johannes, P.T.W. et al. XP002048806. "Aspergillus as a host for heterologous protein production: the problem of proteases". Tibtech Jul. 1997 (vol. 15). pp. 256–263.
Jarai, G. et al. XP002077528. Abstract for "Nitorgen, carbon, and pH regulation of extracellular acidic proteases of Aspergillus niger". Current Genetics 26 (3). 1994. pp. 238–244.
XP 002048808. Abstract for "Enzyme compositions useful preparation hydrolysis food protein contain prolyl endo peptidase obtain mircrobe pseudomonas species". May 9, 1995.

*Primary Examiner*—Remy Yucel
*Attorney, Agent, or Firm*—Pennie & Edmonds LLP

[57] ABSTRACT

The present invention has for an object a koji mold which expresses at least 2 times more endo- and exo-peptidases than the wild type strain of *Aspergillus oryzae* CNCM I-1882, and especially at least 30 mU of endopeptidase activity, at least 30 mU of leucine-amino-peptidase and at least 10 mU of prolyldipeptidyl-peptidase activity per ml of supernatant when grown in a minimal medium containing 0.2% soy bean proteins. The invention also provides a DNA-binding protein of *Aspergillus oryzae* (AREA) having at least the amino-acid sequence from amino-acid 1 to amino-acid 731 of SEQ ID NO:2 or functional derivatives thereof. The invention also provides a DNA molecule that comprises an areA gene encoding the DNA-binding protein according to the invention. In a fourth aspect, the invention provides a method for over-producing proteolytic enzymes, comprising cultivating a koji mold according to the invention in a suitable growth medium under conditions where the mold expresses enzymes, and optionally isolating the enzymes in the form of a concentrate. In another aspect, the invention provides the a method for hydrolyzing protein-containing materials using the koji mold of the invention. In a last further aspect, the invention provides a food product comprising a protein hydrolysate obtainable by fermentation with a koji mold of the invention of a material comprising proteins and at least 5 mM of L-glutamine.

12 Claims, 4 Drawing Sheets

```
WT    CATCCGTCACGACT.CCGACATCAAGCCGCGC
              |||||||||||||||  ||  |||||||||||
mutant CATCCGTCACGACTTAAGATATCAAGCCGCGC
                                    EcoRV
```

ENHANCED EXPRESSION OF PROTEOLYTIC ENZYMES IN KOJI MOLD

TECHNICAL FIELD

The invention relates to genetic modifications of koji molds allowing enhanced expression of proteolytic enzymes.

BACKGROUND OF THE INVENTION

Hydrolyzed proteins, which are widely used in the food industry, may be prepared by hydrolysis of protein material with acid, alkali or enzymes. Various methods have been used koji molds for the preparation food products, which are hydrolyzed by action of a large variety of secreted amylases, proteinases and peptidases. Koji molds are those traditionally used for making a koji culture (U.S. Pat. No. 4,308,284) including cells of the genus Aspergillus, Rhizopus and/or Mucor, especially Aspergillus soyae, Aspergillus oryzae, Aspergillus phoenicis, Aspergillus niger, Aspergillus awamori, Rhizopus oryzae, Rhizopus oligosporus, Rhizopus japonicus, Rhizopus formosaensis, Mucor circinelloides, Mucor japanicus, Penicillium glaucum and Penicillium fuscum, for example.

According to the rules of the International Code of Botanical Nomenclature (ICBN), Aspergillus is an anamorphic genus. This means that true Aspergillus only reproduce asexually through conidiophores. However, the typical Aspergillus conidiophore morphology can also be found in fungi that can reproduce sexually via ascospores. Some Aspergillus taxonomists caused confusion, because they did not adhere to ICBN terminology. Instead, they attempted to make various revisions of taxonomical schemes to include Aspergillus nidulans in this genus, despite the fact that its taxonomically correct name is Emericelia nidulans (Samson, In: Aspergillus. Biology and Industrial Applications, pp 355–390, Ed. by Bennett and Klich, Boston)

EP417481 (Société des Produits Nestlé) thus describes a process for the production of a fermented soya sauce, in which a koji is prepared by mixing a koji culture with a mixture of cooked soya and roasted wheat, the koji is then hydrolyzed in aqueous suspension for 3 to 8 hours at 45° C. to 60° C. with the enzymes produced during fermentation of the koji culture, a moromi is further prepared by adding sodium chloride to the hydrolyzed koji suspension, the moromi is left to ferment and is then pressed and the liquor obtained is pasteurized and clarified.

EP429760 (Société des Produits Nestlé) describes a process for the production of a flavoring agent in which an aqueous suspension of a protein-rich material is prepared, the proteins are solubilized by hydrolysis of the suspension with a protease at pH6.0 to 11.0, the suspension is heat-treated at pH 4.6 to 6.5, and the suspension is ripened with enzymes of a koji culture.

Likewise, EP96201923.8 (Société des Produits Nestlé) describes a process for the production of a meat flavor, in which a mixture containing a vegetal proteinaceous source and a vegetal carbohydrates containing source is prepared, said mixture having initially at least 45% dry matter, the mixture is inoculated with a koji culture and by one or more another species of microorganisms involved in the traditional fermentation of meat, and the mixture is incubated until meat flavors are formed.

However, on the one hand, acid or alkaline hydrolysis can destroy the essential amino acids produced during hydrolysis thus reducing the nutritional value, whereas enzymatic hydrolysis rarely goes to completion so that the hydrolyzed protein contains substantial amounts of peptides. The optimization and further development of koji processes have been seriously hampered by the lack of knowledge on the nature of the hydrolytic enzymes, their regulation and how process parameters affect their expression and activity (e.g. temperature, pH, water activity, and salt concentration).

In the fungal Emericella nidulans (Katz et al., Gene, 150, 287–292, 1994), fermentation activity is subject to at least three general control circuits including carbon catabolite repression, nitrogen and sulfur metabolite repression. These three regulatory circuits ensure that the available nitrogen-, carbon-, and sulfur sources in a substrate are utilized sequentially according to their nitrogen, energy and sulfur yield. Nitrogen metabolite repression is exerted by the areA gene product in Emericella nidulans (Arst et al., Mol. Gen. Genet., 26, 111–141, 1973), whereas in the other fungals Neurospora crassa (Davies et al., Proc. Natl. Acad. Sci. USA, 84, 3753–3757, 1987), Penicillium chrysogenum (Haas et al., Curr. Genet., 27, 150–158, 1995) and Saccharomyces cerevisiae (Minehart et al., Mol. Cell. Biol., 11, 6216–6228, 1991) similar genes exert a similar function.

The areA gene encodes a positively acting DNA-binding protein (AREA), belonging to the GATA family of transcription factors, that is required for the utilization of all nitrogen sources except ammonia or L-glutamine. Under nitrogen de-repressed conditions, signaled by high intracellular levels of glutamine, areA expression is down regulated by three mechanisms: 1) the AREA protein is inactivated, 2) areA transcription is halted and 3) by action of the 3' untranslated trailer sequence (3'-UTS) areA mRNA degradation is enhanced (Platt et al., EMBO J., 15, 2791–2801, 1996). In the absence of a functional AREA protein, only ammonia or L-glutamine can be utilized as nitrogen source. Consequently, loss-of-function areA mutants can utilize only ammonia or L-glutamine as nitrogen sources (Arst et al., 1973).

Observations in koji fermentation suggest that nitrogen metabolite repression is a major parameter in koji fermentation. For instance, high levels of L-glutamine are shown to negatively affect proteolytic activity in koji fermentation.

Furthermore, it has been observed that high levels of proteolytic activity and glutaminase activity are two mutually exclusive conditions in koji fermentation (Ushijima et al., Agric. Biol. Chem., 51, 1051–1057, 1997). For instance, addition of 25 mM L-glutamine into a minimal growth medium containing 0.1% wheat gluten reduces endoproteolytic enzyme activity about 40–50 fold. This phenomenon may be explained by postulating that L-glutamine is necessary for the induction of glutaminase. However, since L-glutamine is also the effector of nitrogen metabolite repression, the expression of proteolytic enzymes is suppressed when glutaminase is induced.

With regard to the fact that glutaminase suitably converts L-glutamine into L-glutamic acid which is an important natural taste enhancer (see WO95/31114), there is hence a need to overcome L-glutamine mediated suppression of proteolytic enzymes, allowing simultaneous expression of glutaminase and proteolytic enzymes in koji molds.

In addition, depending on the nature of the protein and the enzymes used for proteolysis, the peptides formed can however have extremely bitter tastes and are thus organoleptically undesirable. There is hence also a need for methods of hydrolyzing proteins leading to high degree of protein hydrolysis and to hydrolysates with excellent organoleptic properties.

Finally, biochemical analysis of residual peptides in cereals hydrolyzed by koji molds, e.g. wheat gluten, shows that a considerable amount of L-glutamine remains sequestered in proline containing peptides (Adler-Nissen, In: Enzymatic hydrolysis of food proteins. Elsevier Applied Sciences Publishers LTD, p120, 1986). There is hence also a need for methods of hydrolyzing proteins leading to liberation of high amount of L-glutamine.

SUMMARY OF THE INVENTION

The present invention has for object a koji mold which is capable to expressing at least 2 times more endo- and exo-peptidases than the wild type strain *Aspergillus oryzae* CNCM I-1882, and especially at least 30 mU of endopeptidase activity, at least 30 mU of leucine-amino-peptidase activity and at least 10 mU of prolyl-dipeptidyi-peptidase activity per ml of supernatant when grown in a minimal medium containing 0.2% soy bean proteins.

In a second aspect, the invention also provides a DNA-binding protein of *Aspergillus oryzae* (AREA) having at least the amino-acid sequence from amino-acid 1 to amino-acid 731 of SEQ ID NO:2 or functional derivatives thereof.

In a third aspect, the invention provides a DNA molecule that comprises an areA gene encoding the DNA-binding protein according to the invention.

In a fourth aspect, the invention provides a method for over-producing proteolytic enzymes, comprising cultivating a koji mold according to the invention in a suitable growth medium under conditions that the mold expresses enzymes, and optionally isolating the enzymes in the form of a concentrate.

In another aspect, the invention provides the use of the koji mold of the invention to hydrolyze protein-containing materials.

In a last further aspect, the invention provides a food product comprising a protein hydrolysate obtainable by fermentation with a koji mold of the invention of a material comprising proteins and at least 5 mM of L-glutamine.

DETAILED DESCRIPTION OF THE INVENTION

Within the following description, the percentages are given by weight except where otherwise stated. The amino acid or nucleotide sequences referred as "SEQ ID NO:" are always presented in the sequence listing hereafter. One leucine-aminopeptidase enzyme unit is defined as the amount of enzyme which produces 1 µmol p-nitroaniline per minute at 37° C. from the substrate leucine-p-nitroanilide (absorption measured at 400 nm; $\epsilon=10,500$ $M^{-1}cm^{-1}$). One prolyl-dipeptidyl-peptidase enzyme unit is defined as the amount of enzyme which produces 1 µmol p-nitroaniline per minute at 37° C. from the substrate Alanine-Proline-p-nitroanilide (absorption measured at 400 nm; $\epsilon=10,500$ $M^{-1}cm^{-1}$). One endopeptidase enzyme unit is defined as the amount of enzymes which produces 1 µmol of TCA-soluble peptides per minute at 37° C. from the resorufin-labeled casein substrate under prescribed conditions (Boehringer Cat No. 1080733; absorption measured at 574 nm).

The term "koji" is defined as the product of the fermentation with a koji mold culture of a mixture of a source of proteins and a source of carbohydrates, especially of a mixture of a leguminous plant or of a cooked oleaginous plant and of a cooked or roasted cereal source, for example of a mixture of soya or cooked beans and of cooked or roasted wheat or rice.

Likewise, the expression "functional derivative of an enzyme" includes all amino acid sequences which differ by substitution, deletion, addition of some amino acids, for instance 1–20 amino acids, but which keep their original activities or functions. The selection of a functional derivative is considered to be obvious to one skilled in the art, since one may easily creates variants of the truncated AREA protein (see SEQ ID NO:2) by slightly adapting methods known to one skilled in the art, for instance the methods described by Adams et al. (EP402450; Genencor), by Dunn et al. (Protein Engineering, 2, 283–291, 1988), by Greener et al (Strategies, 7, 32–34, 1994), and/or by Deng et al. (Anal. Biochem, 200, 81, 1992).

In particular, a protein may be generally considered as a derivative of another protein, if its sequence is at least 85% identical to the protein, preferably at least 90%, in particular 99%. In the context of the present disclosure, the identity is determined by the ratio between the number of amino acids of a derivative sequence which are identical to those of the truncated AREA protein (see SEQ ID NO:2) and the total number of or amino acids of the derivative sequence.

The present invention thus concerns any koji molds providing an enhanced expression of proteolytic enzymes, leading to high degree of protein hydrolysis and to hydrolysates with excellent organoleptic properties. Accordingly, these koji molds express (1) high levels of endopeptidases such as those capable to produce TCA-soluble peptides at 37° C. from casein, and (2) high levels of exo-peptidases such as the leucine-amino-peptidase that eliminates N-terminal leucines (Deng et al., Anal. Biochem., 200, 81, 1992) and the prolyl-dipeptidyl-peptidase which eliminates N-terminal X-Proline dipeptides, wherein X may be any amino-acid (Barrett et al., In Mammalian Proteases: A Glossary and Bibliography, N.Y., Acad. Press, 2, p.132, 1986).

With regard to the fact that koji molds of the invention provide an enhanced prolyl-dipeptidyl-peptidase activity, they may suitably be used for liberating L-glutamine remains sequestered in proline containing peptides.

Koji molds providing the following enhanced expression of proteolytic enzymes are particularly adapted for the purpose of the invention: at least about 30 mU/ml*, preferably at least about 50 mU/ml* of endopeptidase activity; at least about 30 mU/ml*, preferably at least about 50 mU/ml* of leucine-amino-peptidase activity; and at least 10 mU/ml*, preferably at least about 15 mU/ml* of proline-dipeptidyl-peptidase activity (* per ml of supernatant when grown in a minimal medium containing 0.2% soy bean proteins).

In addition, koji molds that overcome L-glutamine mediated suppression of proteolytic enzymes, allowing simultaneous expression of glutaminase and proteolytic enzymes, are also part of the invention. These koji molds thus may express the above-mentioned proteolytic activities when grown in a minimal medium containing 0.2% soy bean proteins and at least 5 mM L-glutamine (0.073% w/w), for instance.

Koji molds of the invention may be obtained by random UV and/or chemical mutagenesis, followed by selection of mutagenized koji mold providing the required phenotypic characteristics.

Selection of mutagenized koji mold particularly containing a mutagenized areA gene which is not repressed, when the mutagenized mold is grown in a minimal medium containing repressive amounts of L-glutamine, suitably achieved the needs of the present invention. To this end, areA mutants may be easily selected by classical random mutagenesis (V, chemical) and selection on plates containing about 100 mM methyl ammonium chloride and 0.2% soy protein, for example.

It has to be noted that the prolyl-dipeptidyl-peptidase activity that is not naturally controlled by the areA gene expression, is enhanced against all expectations when the areA gene is de-repressed. Since expression of the prolyl-dipeptidyl-peptidase activity is induced by peptides (unpublished results), this AREA-dependent increase in activity may in fact be caused by the enhanced liberation of peptides by the endoproteases that are under areA control.

With regard to the fact that random UV and/or chemical mutagenesis is time consuming, it would be also more adequate to construct koji molds of the invention by recombinant technology. Accordingly, a koji mold of the invention may preferably contain a recombinant areA gene which is truncated so as the C-terminally truncated AREA protein remains functional but not repressed when the mold is grown in a minimal medium containing repressive amounts of L-glutamine. It has to be noted that this truncation leads also to an areA mRNA that is less sensitive to mRNA degradation.

Truncation may be effected by cutting the native areA gene to a pre-determined region, and by introducing a terminater region thus allowing transcription of a truncated areA mRNA. Truncation is preferably effected downstream of the sequence encoding the DNA binding domain of AREA, that can be easily identified by 17 amino acid loop bound two pairs of cysteine residues. More precisely, truncation may be effected downstream of the areA sequence encoding the conservative amino-acid structure cysteine-2X-cysteine-17X-cysteine-2X-cysteine, where in X is any amino-acids and the numbers 2 and 17 refer to the number of amino-acids (Caddick et al., Antonie van leeuwenhoek, 65, 169–177, 1994). This truncation may be particularly carried out in the 100 amino-acids following the areA sequence encoding the DNA binding domain.

Any functional fungal areA gene may be used in the context of the present invention, and in particular any functional areA gene capable of hybridizing under stringent conditions to the areA gene of *Aspergillus oryzae* having the nucleotide sequence from nucleotide 1189 to nucleotide 3846 of SEQ ID NO: 1 or functional derivatives thereof due to the degeneracy of the genetic code.

A functional areA gene may be obtained in substantially purified form by using the method described within the following examples from any strain of *Aspergillus oryzae*. Alternatively, an areA gene may be (1) detected also from other genera or species of fungals by use of DNA probes derived from the nucleotide sequence SEQ ID NO:1 in a stringent hybridization assay, and (2) recovered by the well known Reverse-PCR method by use of suitable primers derived from SEQ ID NO:1 encompassing the areA gene. In a further aspect, an areA gene may also be in-vitro synthesized and then multiplied by using the polymerase chain reaction, for instance.

A suitable truncated areA gene thus may particularly consist of the nucleotide sequence defined by nucleotides 1189–1604 and 1704–3480 of SEQ ID NO:1 (SEQ ID NO:1 contains an intron) or functional derivatives thereof due to the degeneracy of the genetic code, for example. This truncated gene thus encodes for the AREA DNA-binding protein of *Aspergillus oryzae* having the amino-acid sequence from amino-acid 1 to amino-acid 731 of SEQ ID NO:2, that is required for the utilization of all nitrogen sources except ammonia or L-glutamine.

This truncated areA gene then may be introduced in a vector, e.g. a replicative plasmid or an integrative circular or linearized non replicative plasmid, and may be operably linked to regulatory sequences that regulate a different gene in the said organism of origin or that regulate a different gene in a foreign organism (promoter and/or a terminator), for example. A regulatory sequence other than the native regulatory sequence will generally be selected for its high efficiency or desirable characteristic, such as, in case of a promoter inducibility or high expression capacity, for example.

If heterologous expression is preferred, meaning that the gene of the invention is expressed in another organism than the original host (strain, variety, species, genus, family, order, class or division) the regulatory sequences are preferably derived from an organism similar or equal to the expression host. For example, if the expression host is an Aspergillus, then the regulatory sequences will be derived from Aspergillus. The promoter suitable for constitutive expression, preferably in a fungal host, may be a promoter from the following genes: glycerolaldhehyde-3-phosphate dehydrogenase, phospho-glycerate kinase, triose phosphate isomerase and acetamidase, for example. Promoter suitable for inducible expression, preferably in a fungal host, may be a promoter from the following genes: endoxylanase IIA, glucoamylase A, cellobiosehydrolase, amylase, invertase, alcohol dehydrogenase and amyloglucosidase. The selection of a desirable regulatory sequence operably linked to a sequence of the invention and capable of directing the expression of the said nucleotide sequence is considered to be obvious to one skilled in the art.

The vector may also comprise a selection marker to discriminate host cells into which the recombinant DNA material has been introduced from cells that do not comprise the said recombinant material. Such marker genes are, for example in case fungal expression is preferred, the known ga-2, pyrg, pyr4, pyrA, trpC, amdS or argB genes. The DNA molecule may also comprise at least one suitable replication origin. Suitable transformation methods and suitable expression vectors provided with a suitable transcription promoter, suitable transcription termination signals and suitable marker genes for selecting transformed cells are already known in the literature for many organisms including different Aspergillus, Rhizopus and Mucor. In the event fungal expression is required, the expression system described in EP278355 (Novartis) may be thus particularly adapted.

Recombinant koji molds may be obtained by any method enabling a foreign DNA to be introduced into a cell. Such methods include transformation, electroporation, or any other technique known to those skilled in the art.

In the context of the present invention, koji molds are those traditionally used for making a koji culture including cells of the genus Aspergillus (ICBN taxonomy), Rhizopus and/or Mucor. Among those, the following species may be used, including *Aspergillus soyae, Aspergillus oryzae* (ATCC 20386), *Aspergillus phoenicis* (ATCC 14332), *Aspergillus niger* (ATCC 1004), *Aspergillus awamori* (ATCC 14331), *Rhizopus oryzae* (ATCC 4858), *Rhizopus oligosporus* (ATCC 22959), *Rhizopus japonicus* (ATCC 8466), *Rhizopus formosaensis, Mucor circinelloides* (ATCC 15242), *Mucor japanicus, Penicillium glaucum* and *Penicillium fuscum* (ATCC 10447). Strains referred by an ATCC number are accessible at the American Type Culture Collection, Rockville, Md. 20852, US. The invention is not limited by such indications that were rather give to enable one skilled in the art to carry out the invention.

Recombinant cells of the invention may comprise the truncated areA gene stably integrated into the chromosome or on a replicative plasmid. Among all recombinant cells of the invention thus created, the present invention has particularly for object the strains A. oryzae CNCM I-1881, CNCM I-1883 and CNCM I-1884.

Preferably, only one functional truncated areA gene is integrated into the chromosome under the control of regulatory sequences that are native to the host organism.

In order to stably integrate into the chromosome of eucaryotic cells only one functional truncated areA gene which is fused to a promoter and a terminator which are native to the host organism, the DNA molecule of the invention may be integrated by slightly adapting the process of Ruiter-Jacobs et al. (Curr. Genet., 16, 159–163, 1989), i.e., (1) preparing a non-replicative DNA fragment by ligating the truncated areA gene, which is operably linked to a promoter and terminator that are native to the host organism, downstream the DNA sequence encoding an essential gene, said gene being inactivated by at least one mutation and/or one deletion (this essential gene may be any genes involved in RNA synthesis, such as the pyrG gene in case A. oryzae is used, for example); (2) selecting a host organism containing the essential gene which is however inactivated by another mutation(s) or deletion(s); (3) transforming said host organism with the non replicative DNA fragment; (4) identifying integrate transformants in which the DNA fragment is integrated so as to restore the native function of the essential gene; (5) selecting an integrate transformant in which only one DNA fragment is integrated. Over-expression of the AREA DNA-binding protein may be obtained by incorporation of the truncated areA gene in an expression host, said areA gene being operably linked to one or more regulatory sequences which serve to increase expression levels of the AREA protein of the invention.

The over-expression can be further achieved by introducing (replicative plasmid) or integrating (by integration in the genome) multiple copies of the functional truncated areA gene of the invention. As examples of koji molds containing multiple copies of a functional truncated areA genes, the transformants *Aspergillus oryzae* A (see example 1), *Aspergillus oryzae* xprD1 (see example 3) and *Aspergilus oryzae* NF1 containing pNFF68 (see example 4) were deposited under the Budapest Treaty where they respectively receive the deposit numbers CNCM I-1881, CNCM I-1883 and CNCM I-1884.

The invention is also directed to a process for over-producing proteolytic enzymes comprising, providing koji mold of the invention in a suitable growth medium under conditions that the mold expresses proteolytic enzymes, and optionally isolating the enzymes in the form of a concentrate, for example by removing solids from the fermentation broth by centrifugation or filtration. The selection of the appropriate medium may be based on the choice of expression host and/or based on the regulatory requirements of the DNA recombinant material. Such media are well-known to those skilled in the art. After fermentation, the molds can be removed from the fermentation broth by centrifugation or filtration.

Typical L-glutamine concentrations reached during koji hydrolysis in liquid system may be 0.5–1% w/w, for example. The present koji molds are thus particularly adapted for hydrolyzing any protein containing materials, in particular those containing high amounts of L-glutamine (more than 5 mM). These protein containing materials may be mixtures of a source of proteins and a source of carbohydrates, especially a mixture of a leguminous plant or of a cooked oleaginous plant and of a cooked or roasted cereal source, for example a mixture of soya or cooked beans and of cooked or roasted wheat or rice.

Compositions containing wheat gluten are particularly adapted for the purpose of the present invention, since high amounts of L-glutamine remains sequestered in proline containing peptides when wheat gluten is hydrolyzed by traditional koji cultures.

In the event one may try, after or during hydrolysis with koji molds, to further liberate as much as possible L-glutamine linked to proline residues, the present invention provides a method in which the koji mold of the invention of the invention is used in combination with at least an enzyme or a microorganism providing a prolidase activity, that is to say an enzyme which has a high level of specificity towards dipeptides of the X-Pro type (Ezespla et al., Ap. Env. Microb., 63, 314–316, 1997; Such kind of enzyme is already available from Sigma: E.C. 3.4.13.9).

In addition, the koji molds of the invention are particularly adapted for hydrolyzing protein containing materials that comprise at least 5 mM of L-glutamine, allowing formation of L-glutamic acid which is an important natural taste enhancer and high degree of protein hydrolysates with excellent organoleptic properties.

In a further aspect, the present invention relates to food product comprising a protein hydrolysate obtainable by fermentation of a material comprising proteins and at least 5 mM of L-glutamine with a koji mold of the invention. Such food contains naturally high amounts of L-glutamic acid (and/or L-glutamate) and high degree of protein hydrolysates with excellent organoleptic properties leading to a non-bitter flavor and a significantly lower allergenicity than unhydrolyzed proteins Important food product of the present invention is an ingredient of a mother milk substitute for infants, or a hydrolyzed vegetable protein ingredient. The milk substitute may be further formulated in substantially the same way as that indicated in the prior literature for products of this type (cf. EP 96202475.8).

The present invention is not to be limited in scope by the specific embodiments described herein. Indeed, various modifications of the invention, in addition to those described herein, will become apparent to those skilled in the art from the foregoing description and accompanying figures. Such modifications are intended to fall within the scope of the claims. Various publications are cited herein, the disclosures of which are incorporated by reference in their entireties to the extent necessary for understanding the present invention. DNA manipulation, cloning and transformation of bacteria cells are, except where otherwise stated, carried out according to the textbook of Sambrook et al. (Sambrook et al., Molecular Cloning, A Laboratory Manual, Cold Spring Harbor Laboratory Press, U.S.A., 1989). These examples are preceded by a brief description of the figures, of the plasmids and strains used, and by the composition of various media. The strains *A. oryzae* TK3, *Aspergilus oryzae* A (see example 1), *Aspergilus oryzae* NF2 (see example 2), *Aspergilus oryzae* xprD1 (see example 3) and *Aspergilus oryzae* NF1 containing pNFF68 (example 4) were deposited under the Budapest Treaty, at the Collection Nationale de Culture de Microorganismes (CNCM), 25 rue du docteur Roux, 75724 Paris, France, on Jun. 24, 1997, where they receive respectively the deposit numbers CNCM I-1882, CNCM I-1881, CNCM I-1885, CNCM I-1884, CNCM I-1883. All restrictions as to the availability of these deposits will be withdrawn upon first publication of this application or another application which claims benefit of priority to this application.

FIGURES

STRAINS & PLASMIDS

E. nidulans G 191 (pyrG89, fwnA1, pabaA1, YuA1), E. nidulans G353 (areA1, biA1) and E. nidulans G332 (pabaA1, yA2, xprD1) were obtained from the Glasgow Genetic Stock Center via Dr. A. J. Clutterbuck. Other wild type strains of Emericella nidulans also may have been used in the following examples.

Aspergillus oryzae TK3 was obtained from the strain collection of Nestlé.

Aspergillus oryzae NF1 pyrG1) is a uridine auxotroph derivative of A. oryzae TK3 in which the pyrG gene, encoding orotidine 5'-phosphate decarboxylase, was inactivated by targeted disruption.

Escherichia coli BZ 234 (Collection from the Biozenter, University of Basel, Basel. Switzerland) was used as host for the propagation of plasmids. E. coli strains JM109 (endA1, recA1, gyrA96, hsdR17 ($r_K-$, $m_{K+}$), relA1, supE44, $\lambda^-$, $\Delta$(lac-proAB), [F', traD36, proA$^+$B$^+$, lacI$^q$Z$\Delta$M15]) and EM1301 (lacZ53, mutS201::Tn5, thyA36, rha-5, metB1, deoC, IN(rrnD–rrnE)) were used in the site directed mutagenesis.

The piasmid pHELP1 was used for direct cloning in Emericella nidulans (Gems and Clutterbuck, Curr. Genet., 24, 520–524, 1993; GenBank accession number: X78051).

Plasmid pNFF28 contains the A. oryzae TK3 pyrG gene (GenBank accession number: Y13811).

Plasmid pFBY182, containing the pepB gene as a EcoRI-XbaI fragment under the control of the Aspergillus niger pkiA promoter and terminator was obtained from Novartis, Switzerland, via Dr. Gabor Jarai (GenBank accession number: S38698).

pNEB193 (New England Biolabs), pAlter1 (Promega), pBluescriptSK$^-$ (Stratagene), pHSS19 and pGEM-T (Promega), and pK18 (GenBank accession number: M17626) were used for subcloning.

MEDIA

Fungal Nitrogen Base (FNB) was composed of 1× Yeast Nitrogen Base (YNB) without amino acids and $(NH_4)_2SO_4$ (Difco) with 50 mM glucose as carbon source and 10 mM $NaNO_3$ as nitrogen source. In the case of E. nidulans G353 (areA1, biA1), 10 mM glutamine was added as nitrogen source. Growth tests were performed on MM (which contains per liter 1.5 g $KH_2PO_4$, 0.5 g $MgSO_4.7H_2O$, 0.5 g KCl, Pontecorvo, 1953) only now 10 mM $NaNO_3$ served as sole nitrogen source. Protease plate assays were performed on MM with 0.2% soy protein as sole carbon and nitrogen source. For quantitative studies 250 ml conical flasks filled with 80 ml of MM with 0.2% soy protein, as sole nitrogen and carbon source, were inoculated with $10^6$ conidiospores/ml and incubated for 5 days at 30° C. without agitation.

EXAMPLE 1

Over-expression of the E. nidulans truncated areA gene

To assess the feasibility of increasing expression of proteolytic enzymes by modulation of areA expression, we decided to overexpress the Emericellia nidulans gene in A. oryzae TK3.

Figure 1:
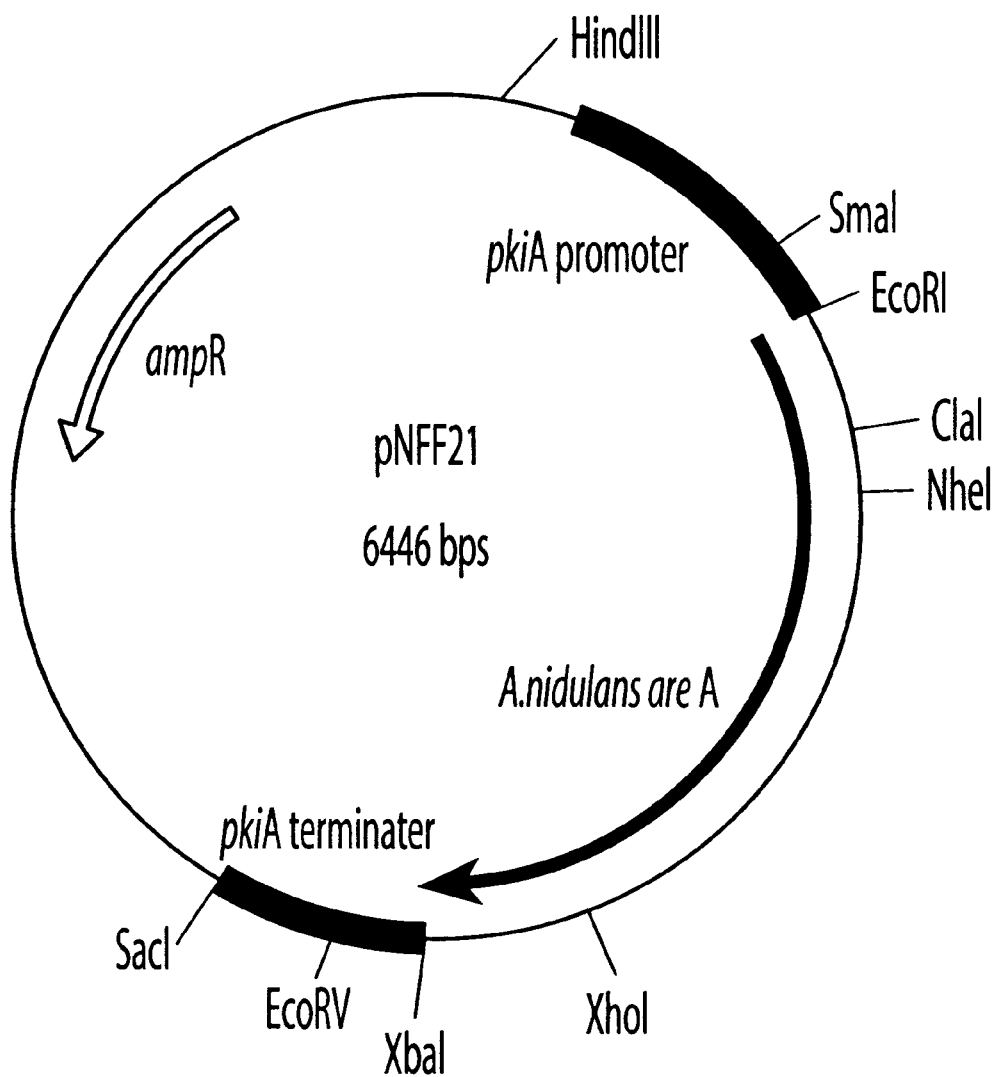
FIG. 1 shows the restriction map of pNFF21 which comprises the truncated E. nidulans areA gene and the pkiA promotor and terminater.

To this end, amplification of the coding region of the areA gene from Emericellia nidulans G191 and cloning of the PCR product into the expression vector pFBY182 were achieved as follows: with oligonucleotides SEQ ID NO:3 and SEQ ID NO:4, a 2,174 bp fragment, encompassing the areA coding region between positions 2009 and 4168, was amplified from genomic DNA of E. nidulans G191. At the same time an EcoRI site was added to 5' end and a XbaI site to the 3' end, allowing directional cloning into EcoRI-XbaI digested fungal expression vector pFBY182 to give pNFF21 (see FIG. 1). In pNFF21, areA transcription is under control of the A. niger pkiA promoter and terminator (Graaff, Curr. Genet., 22, 21–27, 1992), thereby preventing the down-regulation under repressing conditions exerted by its native 3'UTS.

pNFF21 was introduced into A. oryzae NF1 (pyrG1) by co-transformation with pNFF28 containing the A. oryzae pyrg gene. Accordingly, A. oryzae NF1 was grown in MM with 0.1% yeast extract (Difco), 50 mM glucose and 5 mM glutamine. The mycelium was harvested by sterile filtration, washed once with sterile double distilled water and once with K0.8MC (20 mM MES-HCl pH 5.8, 0.8 M KCl, 50 mM $CaCl_2$). 1.5 g of mycelium was resuspended in 20 ml of a filter sterilized 5 mg/ml solution of Novozyme 234 in K0.8MC. The mycelium suspension was incubated at 30° C. for 2 hours with gentle agitation (120 rpm). The protoplasts were liberated from the mycelium by gentle resuspension with a pipet, washed twice with 20 ml of S1.0TC (10 mM Tris-HCl pH 7.5, 1 M Sorbitol, 50 mM $CaCl_2$) and were resuspended in a final concentration of $10^8$/ml in S1.0TC. 20 µl of DNA was mixed with 200 µl of protoplasts and 50 µl of 25% PEG 6000 in 10 mM Tris-HCl pH 7.5, 50 mM $CaCl_2$ and incubated for 20 min on ice. To this mixture, 2 ml of 25% PEG 6000 (BDH) in 10 mM Tris-HCl pH 7.5, 50 mM $CaCl_2$ were added, gently mixed and incubated for 5 min at room temperature. 4 ml of S1.0TC was added and 1.0 ml aliquots were mixed with 5 ml of 2% low melting point agarose (Sigma) in OFNB (osmotically stabilized fungal nitrogen base) and plated onto OFNB agar (Difco) with 50 mM glucose and 10 mM NaNO$_3$. *A. oryzae* NF1 transformants were plated on MM agar with 1 M sucrose, 50 mM glucose and 5 mM glutamine.

The resulting transformants were screened on MM containing 2% soy protein. Among 20 transformants screened, three showed increased secretion of proteolytic activity as judged from the sizes of the halo surrounding the colony after 36 hours of incubation at 30° C. (transformants A, B and C). These three transformants were grown for five days at 30° C. in stationary liquid cultures in MM with 0.2% soy protein and analyzed for proteolytic activity with the appropriate controls.

To this end, conidiospores (10$^6$/ml) of these three strains were used to inoculate 80 ml of liquid MM with 0.2% soy protein as sole nitrogen and carbon source. These cultures were incubated for 5 days at 30° C. without agitation. After filtration to remove the mycelium, the medium was assayed for endoproteolytic activity (Endo), Leucine aminopeptidase activity (Lap) and proline-dipeptidyl-peptidase activity (DPPIV). Endoproteolytic enzyme activity was measured with resorufin-labeled casein according to Boehringer method description supplied with the substrate (Resorufin-labeled casein, Cat.No. 1080733). Leucine aminopeptidase and dipeptidyl peptidase IV activities were determined by UV spectrometry with synthetic substrates Leu-pNa and Ala-Pro-pNa (Bachem, Switzerland), respectively, according to Sarath et al. (In Protease assay methods for proteolytic enzymes: a practical approach, Beynon R. J., Bond J. S., eds., IRL Press, Oxford). 10 mM substrate stock solution in dimethylsulfoxide (DMSO) was diluted with 100 mM sodium phosphate buffer, pH 7.0, to a final concentration of 0.5 mM. 20–100 µl culture medium supernatant was added and reaction proceeded for up to 60 min at 37° C. A control with blank substrate and blank supernatant was assayed in parallel. The release of the chromophoric group 4-nitroaniline ($\epsilon$: 10,500 M$^{-1}$cm$^{-1}$) was measured at 400 nm and activities were expressed as mU/ml (nmol/min/ml).

Figure 2:
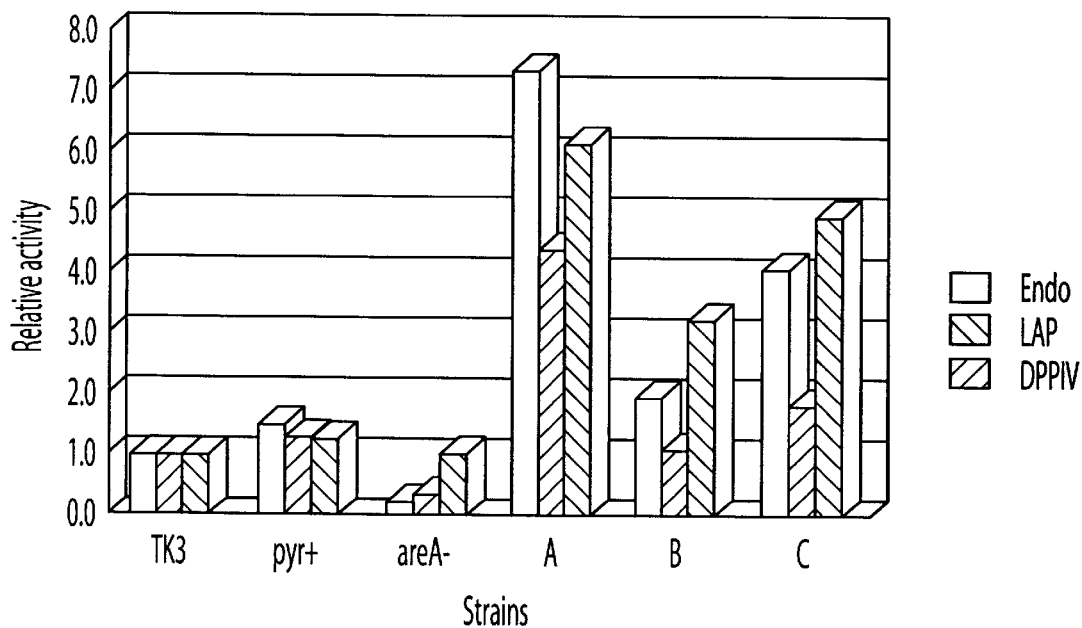
FIG. 2 shows the relative Endo, LAP and DPPIV activities of A. oryzae TK3 (wild type), A. oryzae transformed by pNFF28 encompassing the pyrG gene (control pyr+), A. oryzae areA disruption mutant (control areA-; see example 2), and 3 mutants of A. oryzae NF1 which were cotransformed with pNFF28 and pNFF21.

Relative proteolytic activities are shown in FIG. 2. In the areA disruption mutant endoproteolytic (Endo) and leucine aminopeptidase (Lap) activity are significantly reduced compared to TK3 and the pyr+ control strains, whereas proline dipeptidyl peptidase activity (DPPIV) is not affected. Apparently, proline dipeptidylpeptidase expression is not under areA control. Introduction of multiple copies of *E. nidulans* areA in *A. oryzae* NF1 under the control of the pkiA expression signals results in over-expression of endoproteolytic, leucine aminopeptidase and proline-dipeptidyl-peptidase enzyme activity.

EXAMPLE 2

Over-expression of the *A. oryzae* truncated areA gene

1) Cloning of the *A. oryzae* areA gene: the *A. oryzae* areA gene was cloned by complementation of the corresponding areA gene of *E. nidulans* with the instant library method (Gems et al., 1993).

First of all, the isolation of the genomic DNA was performed according to a modified protocol of the method described by Raeder and Broda (Let. appl. Microbiol., 1, 17–20, 1985). Mycelium was harvested by filtration, immediately frozen in liquid nitrogen and lyophilized. It was then reduced to a fine powder using a mortar and pestle. 200 mg of the powdered mycelium was resuspended in 2.5 ml of extraction buffer (200 mM Tris-HCl pH 8.5 150 mM NaCl, 25 mM EDTA, 0.5% SDS) and the solution was extracted with 1.75 ml extraction buffer-equilibrated phenol and 0.75 ml of chloroform/isoamylalcohol (24:1, v/v). The mixture was centrifuged (20 min, 3000 g). The aqueous phase was retrieved and incubated with 125 µl of RNAse A (Boehringer) solution (10 mg/ml) for 10 min at 37° C. 1.25 ml of 2-propanol (Merck) were then added. The pellet was washed with 70% ethanol and finally resuspended in 500 ml of TE buffer (10 mM Tris-HCl pH 8.0, 1 mM EDTA). 500 ml of 2×QBT (1.5 M NaCl, 100 mM MOPS, 30% ethanol, pH 7.0) were added to the sample which was then applied to a "Genomic-tip 100" (Qiagen), rinsed and eluted as recommended by the supplier.

Cloning by complementation was then achieved by mixing 40 µg BamHI digested pHELP1 with either 100 µg BamHI digested or 100 µg partially Sau3A digested genomic DNA from *A. oryzae* TK3. Additionally, 40 µg KpnI digested pHELP1 was mixed with 100 µg KpnI digested genomic DNA from *A. oryzae* TK3. All three DNA mixes were introduced into *E. nidulans* G332 and transformants were selected on osmotically stabilized FNB medium with NaNO$_3$ as sole nitrogen source.

The transformation experiment with the partially digested Sau3A*A. oryzae* TK3 DNA, did not yield any transformants. By contrast the experiments with the BamHI and KpnI digested *A. oryzae* TK3 DNA did yield 14 and 3 transformants respectively. Again these transformants exhibited irregular growth, which suggested that the complementing gene was located on an autonomously replicating plasmid. In a separate experiment 40 µg KpnI digested pHELP1 was co-transformed with 100 µg KpnI digested genomic DNA from *E. nidulans* G332 (xprD1) and one transformant was obtained.

Figure 3:
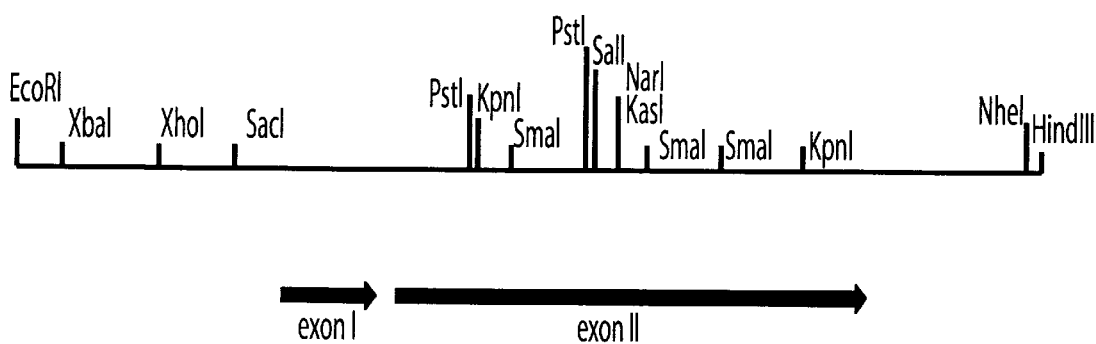
FIG. 3 shows the restriction map of the 4.6 kb EcoRI-HindIII insert of plasmid pNFF5, which complements the areA 19 mutation in Emericellia nidulans G332; both exons encompassing the coding region are indicated with solid arrows.

From three BamHI derived transformants and one KpnI derived area transformant, plasmids were rescued by transformation of *E. coli*. No plasmids could be isolated from the transformant from the xprD1 transformation. From each individual *E. nidulans* BamHI areA$^+$ transformant several plasmids could be recovered. Restriction analysis of these plasmids showed that they were pHELP1 derivatives containing additional restriction fragments, but that not all of these inserts carried terminal BamHI sites. Similarly, from the KpnI areA$^+$ transformant several pHELP1 derivatives could be recovered, non of which had an insert with terminal KpnI sites. These observations indicate instability of the plasmids One BamHI (pNFF3) and one KpnI (pNFF4) pHELP1 derivative were chosen for further analysis. The inserts of both clones hybridized to the coding region of the *E. nidulans* areA gene. Detailed analysis of these two clones showed that in pNFF3, the entire areA gene was located on a 4.6 kb EcoRI-HindIII fragment (FIG. 3). This 4.6 kb EcoRI-HindIII fragment was subcloned into pHSS19 to give pNFF5. Upon re-introduction into *E. nidulans* G323, pNFF5 restores its ability to grow on NaNO$_3$ as sole nitrogen source demonstrating that this plasmid contains a functional areA gene (data not shown).

2) Characterization of the *A. oryzae* areA gene: the complete nucleotide sequence of the EcoRI-HindIII insert of pNFF5 was determined by analysis of both strands on partially overlapping subclones. The nucleotide sequence was determined, on a Licor model. 4000 automatic sequencer. IRD41 labeled primers were used for sequencing both strands of partially overlapping subclones by the dideoxynucleotide method of Sanger et al. (Proc Natl Acad Sci USA, 74, 5463–5467, 1977). The DNA sequence analysis was performed by using the GCG Computer programs (Devereux et al., Nucl. Acids Res., 12, 387–395, 1987).

Results show that the *A. oryzae* areA gene encodes a protein of 853 amino acid residues with a deduced molecular weight of 91.5 kDa (see SEQ ID NO:2). At the protein level the *A. oryzae* areA exhibits a similarity of 83% and at the DNA level 70% similarity with the *E. nidulans* areA gene.

Moreover, in the putative promoter region the overall DNA homology with *E. nidulans* drops to 43%. Still, seven stretches of DNA 5 to 13 bp long show 100% sequence identity and occupy virtually identical positions in both promoters. These sequences could represent cis-acting elements. Additionally, the 5' non-transcribed region contains several putative AREA-binding sites (GATA or TATC; Fu and Marzluf, Proc. Natl. Acad. Sci USA, 87, 5351–5355, 1990) two of which occupy identical positions as the two functional AREA-binding sites in *E. nidulans*.

3) Disruption of the *A. oryzae* areA gene: to elucidate the role of areA in the expression of protease encoding genes, an areA-null mutant was generated by gene disruption. To construct such an areA null allele, the two internal SmaI fragments (see FIG. 3) were removed from pNFF5 to give pNFF10. To do so, pNFF10 was created by digesting pNFF5, containing the *A. oryzae* TK3 areA gene, with SmaI and self-ligating the vector containing fragment. This deleted the internal 0.5 and 0.2 kb SmaI fragments from the second exon of the areA gene in pNFF5.

Figure 4:
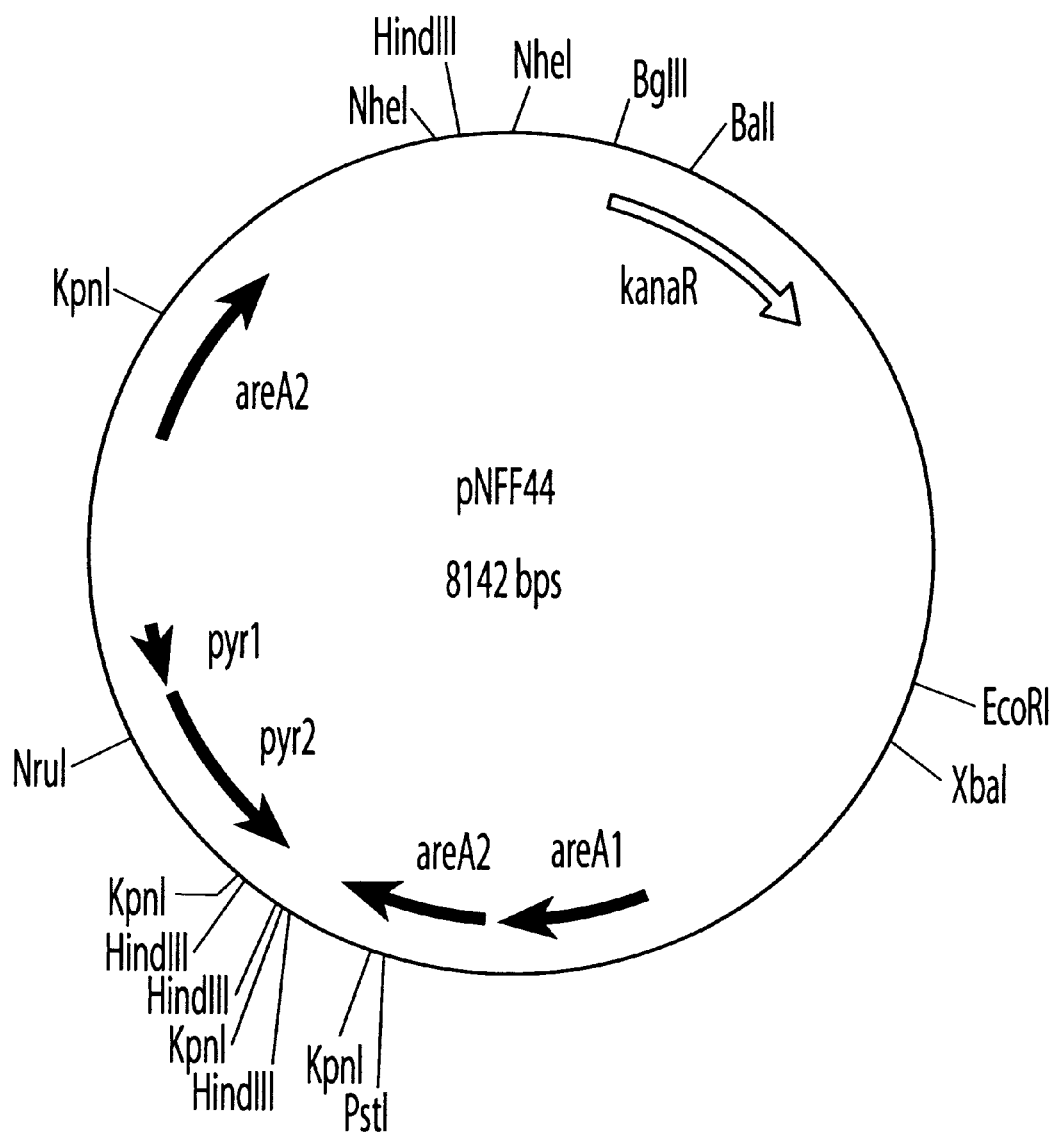
FIG. 4 shows the areA disruption construct pNFF44 containing the two exons of the E. nidulans pyrG gene (pyr1 and pyr2), the two exons of A. oryzae areA gene (areA1 and areA2) and the bacterial kanamycin resistance gene (KanaR).

As selection marker, a PCR product, encompassing the *E. nidulans* pyrG gene, was inserted into the unique SmaI site of pNFF10 to give pNFF44 (FIG. 4). Accordingly, with oligonucleotides SEQ ID NO:5 and SEQ ID NO: 6 the pyrG gene was amplified from *E. nidulans* G332 and the 1.851 bp PCR product cloned into pGEM-T (Promega) to give pNFF38 and pNFF39. The EcoRI fragment, encompassing the pyrG gene was retrieved from pNFF39, blunt ended with T4 DNA polymerase and cloned into the SmaI site of pNFF10.

This pNFF44 construct, linearized with EcoRI and NheI, was used to transform *A. oryzae* NF1, and transform ants were selected on osmotically stabilized MM containing glucose and glutamine as carbon and nitrogen source respectively. All pyrG+ transformants were further checked for their ability to use nitrate and soy protein as sole nitrogen sources. Four pyrG+transformants exhibited greatly reduced or no growth on nitrate MM and three did not form a halo when grown for two days on MM containing 0.2% soy protein as sole nitrogen and carbon source (data not shown). A Southern blot of SmaI digested genomic DNA of these four and six other pyrG+ transformants was digested with SmaI and probed with the 4.6 kb EcoRI-HindIII insert of pNFF5. Only in one of the transformants the two internal SmaI fragments of the areA gene were deleted, identifying this transformant as an areA null-mutant. This areA disruption mutant was called NF2.

The areA mutant NF2 was grown for 5 days at 30° C. without agitation in 80 ml of MM with 0.2% soy protein. The areA mutant grew poorly on MM with 0.2% soy protein. Analysis of the culture broth showed a 75% decrease in total endoproteolytic activity and a 60% decrease in leucine aminopeptidase activity compared to the *A. oryzae* TK3 (WT) control (FIG. 2). By contrast the proline dipeptidylpeptidase activity in the areA mutant did not significantly differ from the wild type control (FIG. 2).

4) Construction of a constitutive areA allele : co-transformation experiments with pNFF5, containing the WT areA gene, did not yield co-transformants that overproduced proteolytic enzymes (data not shown). This suggested tight regulation of the *A. oryzae* areA gene.

To allow the constitutive expression of proteolytic enzymes (i.e. in the presence of glutamine), truncation of the areA gene was achieved. By site directed mutagenesis, a stop codon (TAA), an AflII and an EcoRV site were introduced into the 4.6 kb EcoRI-HindIII areA fragment, truncating the AREA protein after amino acid residue 752 (see FIG. 5).

To this end, the EcoRI-HindIII insert of pNFF5 was ligated into pALTER1 and introduced into *E. coli* JM109 to give pNFF49. By superinfection with the helperphage M13KO7, single stranded DNA was generated from pNFF49 which was used in the site directed mutagenesis procedure with the Altered sites II kit (Promega). Then 0.05 pmol single stranded pNFF49 was annealed to 0.25 pmol Ampicillin repair oligonucleotide SEQ ID NO:7, 0.25 pmol Tetracycline knock-out oligonucleotide SEQ ID NO: 8 and 1.25 pmol areA/xprD1 mutagenic oligonucleotide SEQ ID NO:9, in 20 µl of 20 mM Tris-HCl pH 7.5, 10 mM MgCl$_2$ and 50 mM NaCl in a Perkin Elmer Thermocycler programmed to heat the annealing mixture to 75° C. for 5 min and then to cool to 45° C. at a rate of 1° C/min. From 45° C. to 20° the cooling rate was increased to 1.5° C/min. Next 3 µl 100 mM Tris-HCl pH 7.5, 5 mM dNTPs, 10 mM ATP and 20 mM DTT were added. The mixture was incubated for 90 min at 37° C. with 5U T4 DNA polymerase and 1U T4 DNA ligase. A 3 µl aliquot of the reaction mixture was introduced into *E. coli* ES1301 by electroporation and transformants were selected in 5 ml LB containing 125 µg/ml ampicillin. The mutagenised plasmids were recovered from ES1301 and introduced into BZ234.

The 3.5 kb EcoRI-EcoRV fragment was further cloned into pBluescript to give pNFF58. To test functionality pNFF58 was introduced into *A. oryzae* NF2 (see above) and transformants were selected on OFNB containing NaNO$_3$ as sole nitrogen source. With pNFF58, 1.5 transformants/µg were obtained and with the control pNFF5, 6 transformants/µg. These data prove that pNFF58 still contains a functional areA gene. The pNFF58 transformants were screened for proteolytic activity on MM with 0.2% soy protein and MM with 0.2% soy protein and 10 mM glutamine. On 0.2% soy protein several transformants produced bigger halos that the wild type control (*A. oryzae* TK3) suggesting that overexpression results in enhanced secretion of proteolytic enzymes. Most transformants produced halos on both media, suggesting derepressed expression of proteolytic enzymes (data not shown).

EXAMPLE 3

Construction of protease-overproducing Koji mould strains.

In order to produce potential production koji mold strains, at least one additional copy of the de-repressed areA allele would need to be introduced into the *A. oryzae* TK3 derivative NF1. For regulatory reasons, this had to be done without introducing bacterial sequences, especially antibiotic resistance genes. To this end the inserts of pNFF28 and pNFF58 were amplified by PCR with PfuI DNA polymerase and phosphorylated oligonucleotides SEQ ID NO: 10 and SEQ ID NO: 11. The amplification products were self-ligated and purified. 10 µg of the pNFF58 amplification product and 10 µg of the pNFF28 amplification product were introduced into *A. oryzae* NF1 and the transformants were selected on osmotically stabilized MM with 50 mM glucose and 5 mM glutamine. As a control also 10 µg of pNFF28 was introduced. The plasmid pNFF28 yielded 30 transformants/µg, the pNFF28 PCR product 6 transformants/µg and the pNFF28/pNFF58 PCR products 16 transformants/µg.

Figures 5, 6:
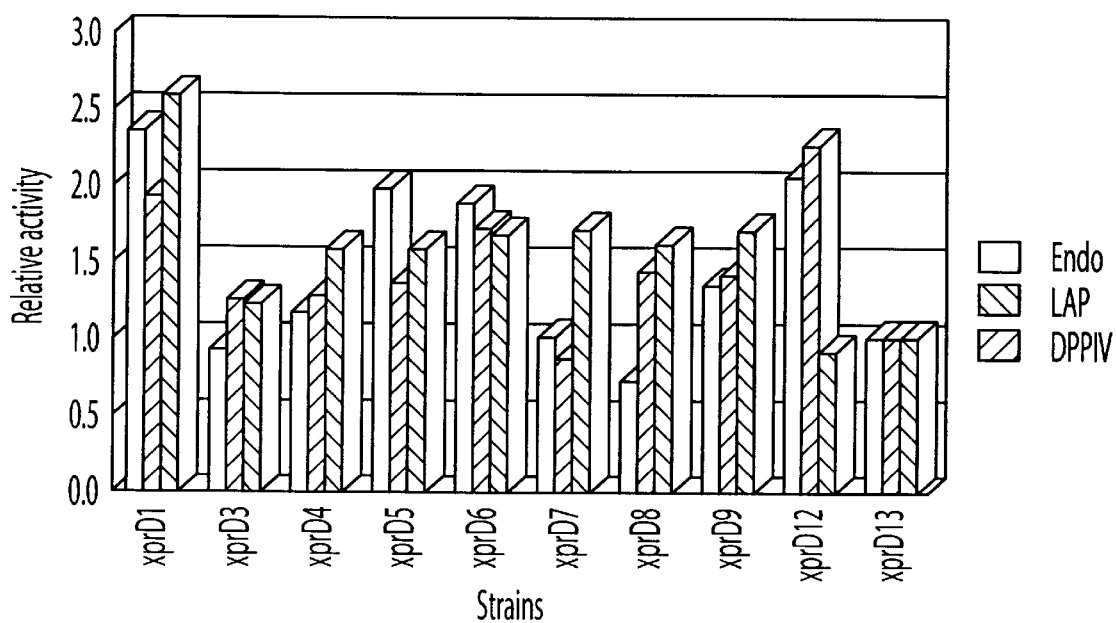
FIG. 5 shows the site directed mutagenesis of the A. oryzae areA gene; the mismatches in the mutagenic primer with the wild type areA sequence are indicted as follows: the stop codon (TAA) is italic, the AflI site doubly underlined and the introduced EcoRV site is marked in bold print and is underlined.
FIG. 6 shows the relative Endo, LAP and DPPIV activities of A. oryzae TK3 (wild type) and 9 mutants of A. oryzae NF1 which were co-transformed with derepressed areA amplification product and the pyrG amplification product. and transformants were selected on MM with glucose and glutamine.

The potential co-transformants were screened for increased protease activity on MM with 0.2% soy protein and MM with 0.2% soy protein and 10 mM L-glutamine. Twelve transformants produced more proteolytic activity on both media as indicated by the increased size of the halo they produced. To quantify the overexpression, nine of them were incubated without agitation for 5 days at 30° C. in 80 ml MM containing 0.2% soy protein. The culture media were assayed for proteolytic activity (FIG. 6).

As with the E. nidulans areA gene under control of the A. niger pkiA expression signals (FIG. 2) all three classes of proteolytic activity tested were increased compared to the A. oryzae TK3 wild type and a pyrG$^+$ derivative of A. oryzae NF1.

Southern analysis of the protease overproducing strains showed that all co-transformants contain 2 to 4 functionally integrated copies of the de-repressed areA gene.

Comparing the observed levels of protease overproduction and the number of functionally integrated copies of de-repressed areA gene, no clear relation was observed. Transformant xprD1 produces the highest level of proteolytic activity and contains multiple copies of functionally integrated xprD1. However, transformant xprD12 contains far less copies of functionally integrated xprD1 but produces almost as much activity as transform ant xprD1. Furthermore, the hybridization patterns of xprD6 and xprD7 are very similar, yet xprD6 overproduces all activities tested 1.5 fold but xprD7 overproduces only proline dipeptidylpeptidase.

EXAMPLE 4

Expression of A. oryzae xprD1 allele with the promoter and terminator of the A. oryzae dppIV gene Co-transformation experiments of example 2 resulted in strains that had muliple copies of pNFF58 integrated in the genome and that overproduced proteolytic activity 2 to 3 fold when compare to the wild type TK3 strain. By contrast, strains with one copy of pNFF21 (example 1), where E. nidulans areA is under the control of a strong glycolytic promoter resulted in 6 fold over-expression. These data suggest that the native areA promoter is a weak promoter and that expression of a functional truncated areA under control of a strong promoter gives better results.

To this end, the dppIV gene of A. oryzae TK3 was amplified by PCR with PfuI DNA polymerase and phosphorylated oligonucleotides SEQ ID NO:12 and SEQ ID NO: 13. The PCR product was then digested with ApaI and EcoRV enzymes. The digested ApaI-EcoRV 4.8 kb fragment was subcloned into pALTER1 (Promega) to give pNFF61. Next pNFF61 was subjected to a site directed mutagenesis according to the protocol of Deng et al. (Anal. Biochem., 200, 81, 1992), using the 5'-phosphorylated mutagenic oligonucleotides SEQ ID NO: 14 and SEQ ID NO:15 according to the manual with Altered sites II kit (Promega) resulting in pNFF62. Using the polymerase enzyme PfuI and the oligonuclotides SEQ ID NO:16 and SEQ ID NO:17, the xprD1 allele was amplified by PCR, from pNFF58 containing the A. oryzae xprD1 allele, as a 3.4 kb EcoRI-EcoRV fragment. The 2294 bp xprD1 amplification product was then phosphorylated and cloned into the SmaI digested vector pK19 (Pridmore et al., Gene, 56, 309–312, 1987) to give pNFF64. Finally the NotI-Ecl136III insert from pNFF64 was inserted into NotI-HpaI pNFF62 creating pNFF68 encompassing the xprD1 allele fused to the dppIV promoter and terminater.

PNFF68 was intoduced into A. oryzae NF1 by co-transformation with pNFF28, and primary transformants were screened for increased proteolytic activity on MM plates containing 0.2% soy protein. Five out of 35 transformants exhibited increased halo sizes compared to A. oryzae TK3. Among the 5 transformants thus selected, one was deposited under the Budapest Treaty at the CNCM, where it received the deposit number CNCM I-1883.

Co-transformants over-expressing proteolytic enzymes and wild type controls were plated on MM plates containing 0.2% soy protein and 5 mM L-glutamine. All the selected co-transformants still produced a halo in the presence of 5 mM glutamine, whereas the wild type did not, indicating de-repressed expression of proteolytic activity.

To quantify the over-expression, transformants were incubated without agitation for 5 days at 30° C. in 80 ml MM containing 0.2% soy protein. The culture media were then assayed for proteolytic activity. Results show an overproduction of proteolytic activity of at least 6 fold when compare to the wild type TK3 strain.

EXAMPLES 5

For preparing a fermented soya sauce, a koji is prepared by mixing an Aspergillus oryzae CNCM I-1883 koji culture with a mixture of cooked soya and roasted wheat, the koji is then hydrolyzed in aqueous suspension for 3 to 8 hours at 45° C. to 60° C. with the enzymes produced during fermentation of the Aspergillus oryzae CNCM I-1 culture, a moromi is further prepared by adding suitable amount of sodium chloride to the hydrolyzed koji suspension, the moromi is left to ferment and is then pressed and the liquor obtained is pasteurized and clarified.

EXAMPLES 6

For producing a flavoring agent, a aqueous suspension of a mixture of cooked soya and roasted wheat is prepared, the proteins are solubilized by hydrolysis of the suspension with a protease at pH6.0 to 11.0, the suspension is heat-trated at pH 4.6 to 6.5, and the suspension is ripened with the prolidase enzyme of Sigma and proteolytic enzymes which have been isolated from a liquid medium fermented by Aspergillus oryzae CNCM I-1881.

What is claimed is:

1. An isolated koji mold which expresses at least 2 times more endo- and exo-peptidases than the wild type strain *Aspergillus oryzae* CNCM I-1882.

2. An isolated koji mold according to claim 1, which expresses at least 30 mU of endopeptidase activity, at least 30 mU of leucine-amino-peptidase activity and at least 10 mU of proline-dipeptidyl-peptidase activity per ml of supernatant when the koji mold is grown in a minimal medium comprising 0.2% soy bean proteins.

3. An isolated koji mold according to claim 1, which expresses the recited proteolytic activities in the presence of at least 5 mM L-glutamine.

4. An isolated koji mold according to claim 1, further comprising an areA gene, which is not repressed when the koji mold is grown in a minimal medium comprising repressive amounts of L-glutamine.

5. An isolated koji mold according to claim 4, further comprising a truncated areA gene which encodes a C-terminally-truncated AREA protein, wherein the C-terminally-truncated AREA protein remains functional, and wherein the C-terminally-truncated AREA protein is not substantially repressed when the koji mold is grown in a minimal medium comprising repressive amounts of L-glutamine.

6. An isolated koji mold according to claim 4, further comprising multiple copies of an integrated areA gene.

7. An isolated koji mold according to claim 5, wherein the truncated areA gene is operably linked to at least one regulatory sequence which directs over-expression of the areA gene.

8. A koji mold according to claim 5, wherein the areA gene has the nucleotide sequence defined by nucleotides 1189–1604 and 1704–3480 of SEQ ID NO:1 or functional derivatives thereof which comprise nucleotide sequences encoding substantially identical amino acid sequences.

9. An isolated koji mold according to claim 1 wherein the koji mold is selected from the group consisting of Aspergillus, Rhizopus and Mucor.

10. A koji mold according to claim 9 wherein the koji mold is selected from the group consisting of *Aspergillus oryzae* strain CNCM I-1881, *Aspergillus oryzae* strain CNCM I-1883 and *Aspergillus oryzae* strain CNCM I-1884.

11. A method for over-producing proteolytic enzymes, comprising the step of cultivating a koji mold according to claim 1 in a suitable growth medium under conditions where the mold expresses proteolytic enzymes.

12. The method of claim 11, further comprising the step of isolating the proteolytic enzymes in the form of a concentrate.

* * * * *

UNITED STATES PATENT AND TRADEMARK OFFICE
CERTIFICATE OF CORRECTION

PATENT NO. : 6,090,607
DATED : July 18, 2000
INVENTOR(S) : Peter Van Den Broek et al.

It is certified that error appears in the above-identified patent and that said Letters Patent is hereby corrected as shown below:

Column 32,
Line 56, change "areA" to -- *are*A --.
Line 60, change "areA" to -- *are*A --.
Line 64, delete "substantially".
Line 68, change "areA" to -- *are*A --.

Column 33,
Line 2, "areA" to -- *are*A --.
Line 5, change "A koji" to -- An isolated koji --; and change "areA" to -- *are*A --.
Lines 7-9, delete "functional derivatives thereof which comprise nucleotide sequences encoding substantially identical amino acid sequences" and insert -- is a nucleic acid having a sequence encoding the same amino acid sequence encoded by nucleotides 1189-1604 and 1704-3480 of SEQ ID NO:1 --.
Line 10, after "claim 1" insert -- , --.
Line 11, change "koii" to -- koji --.
Line 12, change "Aspergillus, Rhizopus and Mucor" to -- *Aspergillus, Rhizopus* and *Mucor* --.

Column 34,
Line 5, change "over-producing" to -- producing --.

Signed and Sealed this

Sixteenth Day of April, 2002

*Attest:*

JAMES E. ROGAN
*Director of the United States Patent and Trademark Office*

*Attesting Officer*

SEQUENCE LISTING (1) GENERAL INFORMATION:

(iii) NUMBER OF SEQUENCES: 17

6,090,607

-continued (2) INFORMATION FOR SEQ ID NO: 1:

(i) SEQUENCE CHARACTERISTICS:
        (A) LENGTH: 4657 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon
        (B) LOCATION:1189..1604

(ix) FEATURE:
        (A) NAME/KEY: intron
        (B) LOCATION:1605..1703

(ix) FEATURE:
        (A) NAME/KEY: exon
        (B) LOCATION:1704..3846

(ix) FEATURE:
        (A) NAME/KEY: misc_feature
        (B) LOCATION:1189..3480
        (D) OTHER INFORMATION:/label= TRUNCATED-AREA
            /note = "AREA IS TRUNCATED IMMEDIATELY
            DOWNSTREAM THE SEQUENCE ENCODING
            A DNA BINDING DOMAIN"

(xi) SEQUENCE DESCRIPTION: SEQ ID NO: 1:

```
GAATTCTCGA CACCCTTAGT ATTGTGGTCC TTGGACTTGG TGCTGCTATA TATTAGCTAA      60
TACACTAGTT AGACTCACAG AAACTTACGC AGCTCGCTTG CGCTTCTTGG TAGGAGTCGG     120
GGTTGGGAGA ACAGTGCCTT CAAACAAGCC TTCATACCAT GCTACTTGAC TAGTCAGGGA     180
CTAGTCACCA AGTAATCTAG ATAGGACTTG CCTTTGGCCT CCATCAGTTC CTTCATAGTG     240
GGAGGTCCAT TGTGCAATGT AAACTCCATG CCGTGGGAGT TCTTGTCCTT CAAGTGCTTG     300
ACCAATATGT TTCTGTTGGC AGAGGGAACC TGTCAACTAG TTAATAACTA GTCAGAAACT     360
AGTATAGCAG TAGACTCACT GTACGCTTGA GGCCCCTCTC TCTCTTTGCA CTGACTGTCA     420
GCCATACCAT AGTATCATCC CGGAATTAAG AAAAAAAAAA AAAAAAAGAA AAAGAAATTA     480
TTCTACCCCC GATCTGGACA AATTATAACC AGGAGAAAAT CAAGCGAAAG AGGGGCAAAG     540
GAGGAGACAC CATTAAAATT GGGTCTGGCT TGATTCATGA CATACATTCG TCGTCTTGAA     600
TTTCAATAGG TACGGACTGA TGCATTCCAC TCGAGCCTTT TTAGCTGCGT GTCCGTCTCC     660
AATCGCACTT CTTTTCTTAT TTCCTTGTGG GATAAATTGA TTATTTACCG TTTCGTTTTC     720
TCTATATTGC GGTGGTGGTG CGACCCATCC AACTATTATT ATTATAATTG GAATTTGATT     780
TGGATTTTGA TTCCTGTGAC GGATCTCAGA CCAAGTGCCT AAACTATAAC TGACTTGGAC     840
CCCCTTCAGA TCCTAGCTTC CCGATTCTTT TCCACCACTG CTGCATCCTC TTCCTGCACG     900
CAGCGTTCGT TTAGGGCGGG TAGACTGGAA TTTATTCCTT GCGCCACGGA CCAATCGCTC     960
CCTCGACGCT CTCATTCCTG CGTCGAGCTC TTTTTCCCTC GACTCTCATT GCTTGCTGGG    1020
CTGGTTCTTG AACCTCTTCA ATCGTCCTTA TCTCTTTCCC CCCATCCGGC CTGTGATTCC    1080
TATCTTTCCT TTTTTTCTTC CCTTTCTTGT TTGATCCCCC CTCCTCCCCG TCTTATCGCC    1140
TACTATCGTG ATCCCCGCCC TTCCCAATAA AGAGTAGGGC GTGTGAACAT GTCCGGGTTA    1200
ACCCTCGGGC GAGGCCCTGG GGGCGTGCGA CCGACTCAAA CCGCAACTTT TACCACCCAC    1260
CACCCGTCCG CCGATGCTGA CCGCCCAAAC AACCTCCCCC CTACCTCCTC GCAGCTGTCC    1320
GATGACTTTT CTTTCGGTTC CCCTCTGAGC CCCGCCGACT CACAGGCCCA TGACGGCCTA    1380
CTTCAGGACT CCCTCTTCCC TGAATGGGGG TCTGGTGCGC CTCGACCCGG CATTGACAGT    1440
```

```
CCGGATGAGA TGCAGAGGCA AGATCCGTTA GCGACTCAAA TATGGAAGCT CTATTCTAGG      1500

ACCAAGGCCC AGTTGCCCAA CCAGGAGCGT ATGGAAAACC TGACCTGGCG GATGATGGCG      1560

ATGAGTTTGA AACGTAAGGA GCGGGAACGT GCTCAACAGT CCATGTAGGT GTTCTCCCTC      1620

TGTAGAGGAA CGGCTGGACC CGCTCATCAT TAATTTTTTT TTGTCTGTGA AGGTTTCCTG      1680

CGAGACGCGG TAGCTGGCCC CAGTGGTATC GCTCAACTGC GCATTTCCGA CCCGCCCGTT      1740

GCCACCGGTA ACCCTCAGTC AACCGACCTG ACCGCCGACC CTATGAACCT CGACGATTTC      1800

ATCGTGCCCT TCGAATCTCC TTCGGACCAC CCCTCGCCCA GTGCCGTCAA GATTTCCGAC      1860

TCCACGGCGT CCGCGGCCAT TCCCATCAAG TCCCGGAAAG ACCAGCTGAG AGATTCTACC      1920

CCGGTGCCGG CCTCGTTCCA CCATCCGGCT CAGGATCAAC GGAAGAACAG TGAATTTGGC      1980

TACGTCCCCC GTCGCGTGCG CAAGACGAGT ATCGACGAGC GTCAATTTTT CTCACTGCAG      2040

GTGCCGACCC GAAAGCGACC GGCCGAATCC TCGCCCCAGG TACCCCCCGT TTCCAACTCG      2100

ATGTTGGCCC ACGATCCGGA CCTCGCTTCC GGCGTGCCCG ATTATGCCTT GGACGCCCCG      2160

TCCTCGGCCT TTGGCTTCCA TCAAGGTAAC CACCATCCGG TCAATCATCA CAACCACACC      2220

TCCCCCGGGG CACCGTTTGG CTTGGATACG TTCGGCCTGG GAGATGATCC AATCTTGCCC      2280

TCCGCGGGCC CCTACCAGTC GCAATTCACC TTCTCACCCA GCGAGTCTCC GATGGCCTCC      2340

GGTCATCCGT TTGCGAACCT CTATTCGCAT ACCCCGGTGG CTTCGTCCCT CAACTCGACG      2400

GATTTCTTCT CTCCACCGCC ATCAGGCTAC CAGTCCACGG CATCCACGCC GCAGCCCACC      2460

TACGACGGGG ACCATTCCGT TTATTTCGAT ATGCCGTCGG GCGACGCGCG CACCCAGCGC      2520

CGCATTCCGA ACTATATTTC GCATCGGTCC AACTTGTCTG CTTCGCTGCA GCCTCGGTAT      2580

ATGTTCAACC AGAACAACCA TGAACAGGCC AGTTCGTCGA CGGTGCATTC GCCGAGCTAC      2640

CCCATTCCCC AGCCGCAACA TGTGGACCCC ACTCAGGTGT TGAACGCCAC CAATTACTCG      2700

ACCGGCAACT CCCACCATAC CGGCGCCATG TTTTCATTTG GAGCCGATTC AGATAACGAG      2760

GATGGCGATG TCATCAGCT GTCCGAGCGG GCTGGTCTGG CGATGCCGAC TGAATATGGG      2820

GACGAGGACG GGTTCTCGTC GGGCATGCAG TGGGATGGGC AGTTCCCGGG CTCCTTCCAT      2880

TCGCTGCCGG GCTTTGGCCC TCAACATCGC AAGCATGTTA CCATCGGGTC CACGGACATG      2940

ATGGACACCC CCGAGGAGTG GAATCACGGT GGCAGTTTGG GTCGGACTCA TGGGTCGGTG      3000

GCTTCGGTCA GTGAGGTGCG CAACCGAGAG CAGGACCCTC GCCGGCAGAA GATTGCGCGC      3060

ACCACGTCCA CCCCCAATAC GGCCCAGCTG TTGCGCCAAA GCATGCACTC TAATAACAAT      3120

ACGTCTCATA CCTCCCCTAA TACGCCGCCC GAGTCCGCCC TGAGCAGCGC AGTTCCGTCC      3180

CGCCCGGCCA GTCCCGGGGG CAGCAAGAAC GGCGACCAAG GCAGCAACGG ACCGACCACC      3240

TGCACGAACT GCTTCACTCA AACCACTCCG CTGTGGCGTC GGAACCCAGA GGGCCAGCCA      3300

CTGTGCAATG CCTGCGGGTT GTTTTTGAAA TTGCACGGTG TCGTGCGCCC TCTGTCCCTG      3360

AAAACGGACG TTATCAAAAA GCGCAACCGT AGCAGTGCCA ACAGCTTGGC GGTTGGGACC      3420

TCCCGTGCGT CGAAGAAGAC AGCCCGCAAG AACTCGGTGC AGCAAGCATC CGTCACGACT      3480

CCGACATCAA GCCGCGCTCA GAATGGGACT TCCGAATCCC CGCCCGCCGG CTTTAGTGCT      3540

GCCGCGGGAC GGTCGAATGG GGTGGTACCC ATTGCCGCCG CTCCTCCGAA GGCAGCTCCC      3600

TCCGCAGCCG CCTCCCCTAG CACGGGCCAG ACCCGCAACC CGATCCAGGC TGCCCCGAAA      3660

CGTCAACGAC GGCTGGAAAA GGCCACGGAG ATGGAAACGG ACGAGGCTAA CAAGTCCGCG      3720

GGAGGCCGAT CCAAGGTGGT GCCTCTGGCA CCCGCCATGC CACCGGCAGC AGCCAATCCG      3780
```

```
GCGAACCATA GTATTGCCGG AGGCCAAGGG GCTAGTCAGG AATGGGAGTG GTTGACGATG    3840

AGTCTGTAAT TGCCGCGCTT ACCTCTCTAC TTCTCTACAC TCGTTTCTTA ATATCTTTCT    3900

TGAACCCCCC CTTATATTTT CCCACCGTTG ATGCTACGCC ATGACCGATA GAGATGATGA    3960

ATACTGCAAC CAATGGAATC TCGCTAGACG AGAGGTGTTA GATGACGTGG CCCGCGATGC    4020

ACTTAATGAG ATACGAGGAG GTGCAATGCG TTGGTTACGC TAGTTTAATG GTAACATGAC    4080

GAGGGATATT CGCTCTGTTA TTTCGGGCTT TGATCTGTTT CAGTCTGCGA TTTAACAGCG    4140

ACTGATCCTC TGCTGTGACA ATACACAGCT TGTCTTGTGG TTCTGTTGTG GCTTTCTGTT    4200

TGTTTGGCTG ATTTGATTTA TGCTTGATAC AATCGCGTCT GTCCGGACCC CGGCCTTTGT    4260

TTTGTTTTCA GTTCTGATTC TTCACTGTTT CTGATTCTCT TGTTCATGTT TTTGATTTGT    4320

TCAAGGCTTG GGGCCGGGCA GAAGTGCGCA TCTCTGCTTT GTGTTTTCCG TCACCGTGCA    4380

TAGACGCTGT ATGTATATGC TACAGCAAGA TTCTACTTAT CCAGTCTGAG CCTGTATTCA    4440

TTGAAGTGTA GCCAGCTGTC GAATGAGCTT TTTGACGATA TTGTTTTGTT GAGTAGTCAA    4500

CAAGTAGTAT CTGTATATTC CGGAGTCTAA GTAAGACACT TGAGAATAAT GTGGAGCTTC    4560

TCGCCCTGTC ATATATCTGA ACGCTAGCCC GTAGGCCGTG AACAAGGGTG ATAAGGATAT    4620

ACTAGCCTAA TGAATTGACG TCATAGCATA TAAGCTT                             4657
```

(2) INFORMATION FOR SEQ ID NO: 2:

(i) SEQUENCE CHARACTERISTICS:
        (A) LENGTH: 853 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Binding-site
        (B) LOCATION: 652-676
        (D) OTHER INFORMATION:/note= "DNA BINDING SITE"

(ix) FEATURE:
        (A) NAME/KEY: Region
        (B) LOCATION:1..731
        (D) OTHER INFORMATION:/note= "TRUNCATED AREA WHICH IS
            STILL ACTIVE BUT NOT REPRESSED BY
            L-GLUTAM..."

(xi) SEQUENCE DESCRIPTION: SEQ ID NO: 2:

```
Met Ser Gly Leu Thr Leu Gly Arg Gly Pro Gly Val Arg Pro Thr
 1               5                  10                  15

Gln Thr Ala Thr Phe Thr Thr His His Pro Ser Ala Asp Ala Asp Arg
                20                  25                  30

Pro Asn Asn Leu Pro Pro Thr Ser Ser Gln Leu Ser Asp Asp Phe Ser
                35                  40                  45

Phe Gly Ser Pro Leu Ser Pro Ala Asp Ser Gln Ala His Asp Gly Leu
        50                  55                  60

Leu Gln Asp Ser Leu Phe Pro Glu Trp Gly Ser Gly Ala Pro Arg Pro
65                  70                  75                  80

Gly Ile Asp Ser Pro Asp Glu Met Gln Arg Gln Asp Pro Leu Ala Thr
                85                  90                  95

Gln Ile Trp Lys Leu Tyr Ser Arg Thr Lys Ala Gln Leu Pro Asn Gln
                100                 105                 110

Glu Arg Met Glu Asn Leu Thr Trp Arg Met Met Ala Met Ser Leu Lys
        115                 120                 125
```

-continued

```
Arg Lys Glu Arg Glu Arg Ala Gln Gln Ser Ile Gly Ile Ala Gln Leu
130                 135                 140

Arg Ile Ser Asp Pro Pro Val Ala Thr Gly Asn Pro Gln Ser Thr Asp
145                 150                 155                 160

Leu Thr Ala Asp Pro Met Asn Leu Asp Asp Phe Ile Val Pro Phe Glu
                    165                 170                 175

Ser Pro Ser Asp His Pro Ser Pro Ser Ala Val Lys Ile Ser Asp Ser
                180                 185                 190

Thr Ala Ser Ala Ala Ile Pro Ile Lys Ser Arg Lys Asp Gln Leu Arg
            195                 200                 205

Asp Ser Thr Pro Val Pro Ala Ser Phe His His Pro Ala Gln Asp Gln
        210                 215                 220

Arg Lys Asn Ser Glu Phe Gly Tyr Val Pro Arg Val Arg Lys Thr
225                 230                 235                 240

Ser Ile Asp Glu Arg Gln Phe Phe Ser Leu Gln Val Pro Thr Arg Lys
                245                 250                 255

Arg Pro Ala Glu Ser Ser Pro Gln Val Pro Val Ser Asn Ser Met
                260                 265                 270

Leu Ala His Asp Pro Asp Leu Ala Ser Gly Val Pro Asp Tyr Ala Leu
            275                 280                 285

Asp Ala Pro Ser Ser Ala Phe Gly Phe His Gln Gly Asn His His Pro
        290                 295                 300

Val Asn His His Asn His Thr Ser Pro Gly Ala Pro Phe Gly Leu Asp
305                 310                 315                 320

Thr Phe Gly Leu Gly Asp Asp Pro Ile Leu Pro Ser Ala Gly Pro Tyr
                325                 330                 335

Gln Ser Gln Phe Thr Phe Ser Pro Ser Glu Ser Pro Met Ala Ser Gly
                340                 345                 350

His Pro Phe Ala Asn Leu Tyr Ser His Thr Pro Val Ala Ser Ser Leu
            355                 360                 365

Asn Ser Thr Asp Phe Phe Ser Pro Pro Ser Gly Tyr Gln Ser Thr
    370                 375                 380

Ala Ser Thr Pro Gln Pro Thr Tyr Asp Gly Asp His Ser Val Tyr Phe
385                 390                 395                 400

Asp Met Pro Ser Gly Asp Ala Arg Thr Gln Arg Arg Ile Pro Asn Tyr
                405                 410                 415

Ile Ser His Arg Ser Asn Leu Ser Ala Ser Leu Gln Pro Arg Tyr Met
                420                 425                 430

Phe Asn Gln Asn Asn His Glu Gln Ala Ser Ser Thr Val His Ser
    435                 440                 445

Pro Ser Tyr Pro Ile Pro Gln Pro Gln His Val Asp Pro Thr Gln Val
    450                 455                 460

Leu Asn Ala Thr Asn Tyr Ser Thr Gly Asn Ser His His Thr Gly Ala
465                 470                 475                 480

Met Phe Ser Phe Gly Ala Asp Ser Asp Asn Glu Asp Gly Asp Gly His
                485                 490                 495

Gln Leu Ser Glu Arg Ala Gly Leu Ala Met Pro Thr Glu Tyr Gly Asp
                500                 505                 510

Glu Asp Gly Phe Ser Ser Gly Met Gln Trp Asp Gly Phe Pro Gly
            515                 520                 525

Ser Phe His Ser Leu Pro Gly Phe Gly Pro Gln His Arg Lys His Val
    530                 535                 540

Thr Ile Gly Ser Thr Asp Met Met Asp Thr Pro Glu Glu Trp Asn His
```

```
545                 550                 555                 560

Gly Gly Ser Leu Gly Arg Thr His Gly Ser Val Ala Ser Val Ser Glu
                565                 570                 575

Val Arg Asn Arg Glu Gln Asp Pro Arg Arg Gln Lys Ile Ala Arg Thr
                580                 585                 590

Thr Ser Thr Pro Asn Thr Ala Gln Leu Leu Arg Gln Ser Met His Ser
            595                 600                 605

Asn Asn Asn Thr Ser His Thr Ser Pro Asn Thr Pro Pro Glu Ser Ala
            610                 615                 620

Leu Ser Ser Ala Val Pro Ser Arg Pro Ala Ser Pro Gly Gly Ser Lys
625                 630                 635                 640

Asn Gly Asp Gln Gly Ser Asn Gly Pro Thr Thr Cys Thr Asn Cys Phe
                645                 650                 655

Thr Gln Thr Thr Pro Leu Trp Arg Arg Asn Pro Glu Gly Gln Pro Leu
                660                 665                 670

Cys Asn Ala Cys Gly Leu Phe Leu Lys Leu His Gly Val Val Arg Pro
                675                 680                 685

Leu Ser Leu Lys Thr Asp Val Ile Lys Lys Arg Asn Arg Ser Ser Ala
                690                 695                 700

Asn Ser Leu Ala Val Gly Thr Ser Arg Ala Ser Lys Lys Thr Ala Arg
705                 710                 715                 720

Lys Asn Ser Val Gln Gln Ala Ser Val Thr Thr Pro Thr Ser Ser Arg
                725                 730                 735

Ala Gln Asn Gly Thr Ser Glu Ser Pro Pro Ala Gly Phe Ser Ala Ala
                740                 745                 750

Ala Gly Arg Ser Asn Gly Val Val Pro Ile Ala Ala Pro Pro Lys
                755                 760                 765

Ala Ala Pro Ser Ala Ala Ser Pro Ser Thr Gly Gln Thr Arg Asn
                770                 775                 780

Pro Ile Gln Ala Ala Pro Lys Arg Gln Arg Arg Leu Glu Lys Ala Thr
785                 790                 795                 800

Glu Met Glu Thr Asp Glu Ala Asn Lys Ser Ala Gly Gly Arg Ser Lys
                805                 810                 815

Val Val Pro Leu Ala Pro Ala Met Pro Pro Ala Ala Asn Pro Ala
                820                 825                 830

Asn His Ser Ile Ala Gly Gly Gln Gly Ala Ser Gln Glu Trp Glu Trp
                835                 840                 845

Leu Thr Met Ser Leu
        850

(2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "OLIGONUCLEOTIDE"

(xi) SEQUENCE DESCRIPTION: SEQ ID NO: 3:

GGAATTCATG AGTGGCATCG C                                              21

(2) INFORMATION FOR SEQ ID NO: 4:

(i) SEQUENCE CHARACTERISTICS:
```

(A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "OLIGONUCLEOTIDE"

(xi) SEQUENCE DESCRIPTION: SEQ ID NO: 4:

TCTAGACTAC AAACTCATCG TC                                                    22

(2) INFORMATION FOR SEQ ID NO: 5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "OLIGONUCLEOTIDE"

(xi) SEQUENCE DESCRIPTION: SEQ ID NO: 5:

GAATTCCATG GTGTCCTCGT CGG                                                   23

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "OLIGONUCLEOTIDE"

(xi) SEQUENCE DESCRIPTION: SEQ ID NO: 6:

GAATTCGAGC CGTCAGTGAG GCTC                                                  24

(2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "OLIGONUCLEOTIDE"

(xi) SEQUENCE DESCRIPTION: SEQ ID NO: 7:

GTTGCCATTG CTGCAGGCAT CGTGGTG                                               27

(2) INFORMATION FOR SEQ ID NO: 8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "OLIGONUCLEOTIDE"

(xi) SEQUENCE DESCRIPTION: SEQ ID NO: 8:

GCCGGGCCTC TTGCGGGCGT CCATTCC                                               27

(2) INFORMATION FOR SEQ ID NO: 9:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "OLIGONUCLEOTIDE"

(xi) SEQUENCE DESCRIPTION: SEQ ID NO: 9:

CATCCGTCAC GACTTAAGAT ATCAAGCCGC GC    32

(2) INFORMATION FOR SEQ ID NO: 10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO: 10:

CACAGGAAAC AGTCACGAC    19

(2) INFORMATION FOR SEQ ID NO: 11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO: 11:

CGTTTTCCCA GTCACGAC    18

(2) INFORMATION FOR SEQ ID NO: 12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO: 12:

GGGCCCGGTA CCCAATTCGC CC    22

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO: 13:

GATATCGGTT TATTGTGGCC G    21

(2) INFORMATION FOR SEQ ID NO: 14:

-continued (i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "OLIGONUCLEOTIDE"

(xi) SEQUENCE DESCRIPTION: SEQ ID NO: 14:

GGTTTTTTCC ACCATGCGGC CGCAAGGTAC GTCAATTC                                    38

(2) INFORMATION FOR SEQ ID NO: 15:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "OLIGONUCLEOTIDE"

(xi) SEQUENCE DESCRIPTION: SEQ ID NO: 15:

GACTTGGAGG AGTAGTTAAC GGCACATCAT TC                                          32

(2) INFORMATION FOR SEQ ID NO: 16:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "OLIGONUCLEOTIDE"

(xi) SEQUENCE DESCRIPTION: SEQ ID NO: 16:

ATGCGGCCGC TAACCCTCGG GCGAGGCCC                                              29

(2) INFORMATION FOR SEQ ID NO: 17:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "OLIGONUCLEOTIDE"

(xi) SEQUENCE DESCRIPTION: SEQ ID NO: 17:

TTAAGTCGTG ACGGATGCTT GC                                                     22